United States Patent [19]

Suzuki et al.

[11] Patent Number: 5,314,877
[45] Date of Patent: May 24, 1994

[54] WATER-SOLUBLE PENTACYCLIC TRITERPENE COMPOSITION AND METHOD FOR PRODUCING THE SAME

[75] Inventors: Hiroshi Suzuki, Tokyo; Sigeru Watano, Yokohama; Tadashi Sasazuka; Taira Tsutsumi, both of Kitami, all of Japan

[73] Assignee: Hokkaido Sugar Co., Ltd., Tokyo, Japan

[21] Appl. No.: 938,235

[22] PCT Filed: Nov. 19, 1991

[86] PCT No.: PCT/JP91/01577

§ 371 Date: Oct. 23, 1992

§ 102(e) Date: Oct. 23, 1992

[87] PCT Pub. No.: WO92/09553

PCT Pub. Date: Nov. 6, 1992

[30] Foreign Application Priority Data

Nov. 21, 1990 [JP] Japan ................ 2-314412

[51] Int. Cl.⁵ .............. A61K 7/16; C07C 62/32; C07C 51/50; A23L 1/03
[52] U.S. Cl. .................. 514/58; 424/48; 424/49; 514/529; 514/557; 514/835; 514/886; 514/894; 536/103
[58] Field of Search .......... 514/58, 529, 557, 835, 514/886, 894; 536/103; 424/48, 49

[56] References Cited

U.S. PATENT DOCUMENTS

| | | | |
|---|---|---|---|
| 3,671,532 | 6/1972 | Carraz et al. | 514/866 |
| 4,146,615 | 3/1979 | Fauran et al. | 424/195.1 |
| 4,228,160 | 10/1980 | Szejtli et al. | 536/103 |
| 4,501,734 | 2/1985 | Tanaka et al. | 424/195.1 |
| 4,524,068 | 6/1985 | Szejtli et al. | 536/103 |
| 4,530,934 | 7/1985 | Clavenna et al. | 514/925 |
| 4,606,911 | 8/1986 | Hayashi et al. | 514/529 |
| 4,727,064 | 2/1988 | Pitha | 514/58 |
| 4,752,606 | 6/1988 | Snyckers et al. | 514/557 |
| 4,844,901 | 7/1989 | Keplinger et al. | 424/195.1 |
| 4,985,248 | 1/1991 | Liu | 514/874 |

FOREIGN PATENT DOCUMENTS 50-31021 3/1975 Japan.
53-15467 2/1978 Japan.
61-36213 2/1986 Japan.
1-290619 11/1989 Japan.

OTHER PUBLICATIONS

Chemical Abstracts, vol. 104, No. 14, 1985, AN-115941r.
Chemical Abstracts, vol. 106, No. 6, 1986, AN-38269q, JP-A-61 233 609, Oct. 17, 1986.
Chemical Abstracts, vol. 106, No. 8, 1986, AN-5565h, JP-A-61 227 517, Oct. 9, 1986.

Primary Examiner—Ronald W. Griffin
Attorney, Agent, or Firm—Oblon, Spivak, McClelland, Maier & Neustadt

[57] ABSTRACT

Disclosed is water-soluble composition made by subjecting pentacyclic triterpene compound belonging to amylin group such as oleanolic acid, ursolic acid and hederagenin to inclusion in cyclodextrins. Though the aforementioned pentacyclic triterpene compound has various pharmacological functions, it has suffered a disadvantage such that it is insoluble in water. However, by subjecting the compound to inclusion in cyclodextrins, the water-soluble composition can be made with maintaining the pharmacological functions, and applied for foods, drinks, toothpaste, gargle and chewing gum, exhibiting the effect of cariostatic.

7 Claims, No Drawings

WATER-SOLUBLE PENTACYCLIC TRITERPENE COMPOSITION AND METHOD FOR PRODUCING THE SAME

TECHNICAL FIELD

This invention relates to water-soluble pentacyclic triterpene compositions which are made soluble in water while preserving the pharmacological function of pentacyclic triterpene compounds (hereinafter, referred to as triterpene), and a method for producing the same.

BACKGROUND ART

Triterpenes are classified into amylin, lupeol, nosterol and squalene groups. These are all compounds which are insoluble in water and soluble in oil, organic solvents or the like.

The triterpenes are widely distributed in throughout the plant kingdom in the form of a free radical and bound with sugar into saponin or with acid into ester. The amylin group of the triterpenes, which is represented by a chemical formula having an OH-radical at the third position and a COOH-radical at the seventeenth position is a compound as represented by the following formula [1]. The compounds thereof are typically oleanolic acid, ursolic acid and hederagenin as concretely shown in Table 1 below.

The oleanolic acid mentioned above is variously found in a beet in the form of saponin and in the leaves of an olive, a green perilla, a jujube, and a ground ivy, the peel of an apple, the germ of a clove and so on. The ursolic acid is obtained from not only fruit such as an apple and a cherry and waxy coat material of the leaf thereof, but also the leaves of the ground ivy, jujube tree and so on. Furthermore, hederagenin is found in hedera helix, the fruit of a soapberry and so on.

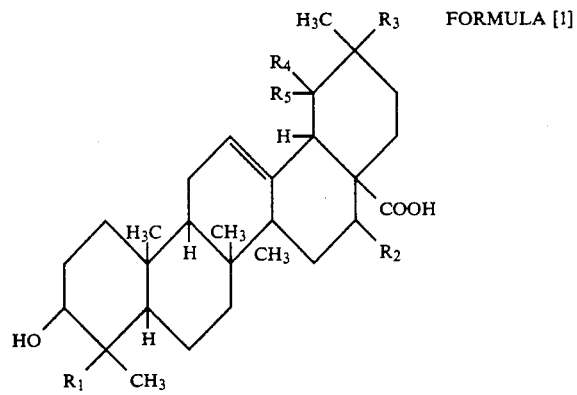

FORMULA [1]

wherein, $R_1$ represents $CH_3$ or $CH_2OH$, $R_2$ represents H or OH, $R_3$ represents H or $CH_3$, $R_4$ represents H or $CH_3$, and $R_5$ represents H or OH.

TABLE 1

| Compound | | $R_1$ | $R_2$ | $R_3$ | $R_4$ | $R_5$ |
|---|---|---|---|---|---|---|
| Amylins | Oleanolic acid | $CH_3$ | H | $CH_3$ | H | H |
| | Ursolic acid | $CH_3$ | H | H | $CH_3$ | H |
| | Pomolic acid | $CH_3$ | H | H | $CH_3$ | OH |
| | Hederagenin | $CH_2OH$ | H | $CH_3$ | H | H |
| | Echinocystic acid | $CH_3$ | OH | $CH_3$ | H | H |

On the other hand, there have been recently carried forward investigations as to substances having pharmacological functions in various plants including medicinal herbs by research laboratories of universities, public and private research institutions and nongovernmental laboratories. Then, it has been confirmed that the amylins of a triterpene group present in a plant, which is represented by a chemical formula having an OH-radical at the third position and a COOH-radical at the seventeenth position, shows pharmacological activity such as antibiosis relative to a tumor, hepatitis, inflammation and caries. Various types of amylin groups have been so far reported in academic societies and in literatures, reviewed in news papers and magazines and proposed by patents.

The inventors of the present invention have also conducted experiments on the pharmacological function of oleanolic acid obtained from a sugar beet and confirmed that the oleanolic acid has the effects of antibiosis to a tumor and hepatitis, cariostatic (insoluble glucanynthesis inhibition) and so on.

Further, as a use of oleanolic acid, there have been proposed compositions for use in the mouth on the basis of the pharmacological function of oleanolic acid (Japanese Patent Publication No. SHO 63-26083).

However, as these triterpenes are insoluble in water, the pharmacological experiments as mentioned above were conducted using specimens obtained by dissolving the triterpene into an organic solvent such as dimethyl sulfoxide (hereinafter referred as to DMSO), ethanol, propylene glycol, and butanediol so as to make the "in vitro" and "in vivo" tests no matter how coarse or fine the triterpene applied therefor is.

There are a good many cases of using particularly DMSO having the high boiling point and high solvent power as the organic solvent applied for the tests as noted above. However, the DMSO is not approved as an additive to foods, drinks or compositions for use in the mouth. Also, the other organic solvents are not satisfactory when being used as a food additive.

Also, the compositions for use in the mouth proposed in the aforenoted Japanese Patent Publication No. SHO 63-26083 do not contain oleanolic acid in the water-soluble state. Therefore, a product obtained from the compositions conventionally proposed shows scarcely the effect of cariostatic and is unmarketably.

One of the inventors of the present invention has proposed a process for producing oleanolic acid from beet pulp (Japanese Patent Application Public Disclosures Nos. SHO 60-268189 and SHO 60-268190), and tried to provide oleanolic acid of high purity with solubility in water weight losing its pharmacological function in order to add oleanolic acid to foods, drinks, compositions for use in the mouth or the like. However, there has not yet been produced the intended compound having high deprived of the pharmacological function of oleanolic acid.

The inventors of the present invention have further proposed a method for producing compositions for use in the mouth by completely dissolving oleanolic acid in ethanol, glycerin, propylene glycol, menthol or the like and combining the solution resultantly obtained with other compositions, on the basis of the fact that oleanolic acid is a little soluble in an organic solvent such as ethanol which is known as a pharmacological solvent (Japanese Patent Appln. Public Disclosure No. HEI 1-290619). However, the proposed method has suffered a disadvantage that compositions thus obtained are unstable in effect, and oleanolic acid contained therein becomes insoluble in water with time.

Also, the pharmacological experiments were carried out by causing oleanolic acid to be dissolved into water or emulsified by use of surface active agents of various types such as fatty ester (nonionics) and ampholytic surface active agent (derived from natural substance). However, the "in vitro" test the inventors conducted reveals that almost all of the surface active agents have no effect of cariostatic. Even in the case of the surface active agents showing a little effect of cariostatic, its effect was remarkably scattered, and moreover, the reproductivity thereof could not been accomplished.

As the result of making the progress in the inventors' elaborate studies, there has been found that a new composition which is soluble in water while keeping the effect of cariostatic shown by the triterpenes in its active condition can be produced by subjecting triterpene having oleanolic acid to inclusion with cyclodextrin (hereinafter referred to as CD).

Though solubilization or emulsification of the triterpenes by use of the surface active agent as touched upon above has been generally accomplished, there has not yet been published a report on a method of subjecting triterpene to inclusion with CD for the purpose of making water-soluble of triterpenes while maintaining the inherent functions of triterpene in its active state.

DESCRIPTION OF THE INVENTION

This invention aims at providing water-soluble pentacyclic triterpene compositions which are produced by subjecting triterpene to inclusion in CD on the basis of the foregoing knowledge, and a method for producing the same, and further providing compositions for use in foods, drinks or compositions for use in the mouth.

Now, CD compositions are utilized for various purposes on the point of function. There has been non-branching type CD compositions such as $\alpha$-CD, $\beta$-CD and $\gamma$-CD which are low in water-solubility. Also, there have been developed, as products largely improved in water-solubility, alkylated CD obtained by making CD into alkyl, hydroxyalkylated CD obtained by making CD into hydroxyalkyl, and branching type CD to which sugar such as glucose and maltose is added. By the development of CD compositions having the functions of stabilizing volatile substance, being stabilized in the form of powder, and making lipophilic substance soluble in water, the CD compositions have been widely applied for foods, and consequently, the demand for the CD compositions continues to expand yearly. The CD composition regardless of the non-branching type or branching type has a spiral structure with an inner hollow. In the inner hollow of the CD composition, the aforenoted triterpene can be subjected to inclusion. Therefore, though there is difference in quantity of triterpene included in the CD, triterpenes of any kind can be subjected to inclusion by and large. Of the CD compositions, the $\gamma$-CD having a large inner hollow or the $\gamma$-CD of the branching type has an advantage in that it can likely include a large quantity of triterpene. Thus, the CD compositions can be selectively applied for various purposes without being restricted in use.

Furthermore, amylins of pentacyclic triterpene compositions according to this invention can be subjected to inclusion in CD, so that the triterpene can be made soluble in water while preserving the activities such as pharmacological function and cariostatic thereof.

The inclusion of triterpene in the CD is achieved in the presence of water. To be more concrete, upon dissolving or suspending the CD in water, triterpene is added thereto and stirred to be subjected to inclusion in the CD.

When subjecting triterpene to inclusion in the CD, though neutral water may be used, it is preferable to use water of weak alkali made by being mixed with sodium hydrogencarbonate, soda ash, caustic soda, caustic potash and so on, thereby to increase the quantity of inclusion of triterpene.

Since triterpene is soluble in organic solvent, it is advisable to prepare the desired triterpene dissolved in a solution of 65% of methanol prior to the inclusion. Then, the CD is added to the solution mixed with the triterpene and stirred to dissolve while being heated. By homogenizing the solution resultantly obtained, the inclusion of triterpene in the CD can be promptly fulfilled.

As the organic solvent applied therefor, there may be used not only methanol, but also ethanol, glyceline, propylene glycol and menthol, for example.

The solvent of inclusion compound of triterpene is subjected to filtration or centrifugation to be cleaned by removing insoluble matter, and then, concentrated and dried by a conventional method to obtain a desired product.

BEST MODE FOR CARRYING OUT THE INVENTION

The embodiments of the present invention will be concretely described hereinafter.

EXAMPLE 1

Upon preparing a suspension of 1 g of $\beta$-CD (made by Ensuiko Sugar Refining Co., Ltd.) in 10 ml of 3% of sodium hydrogencarbonate, 0.2 g of oleanolic acid was added to the suspended solution and stirred at 12,000 rpm for 20 minutes to be homogenized. The solution thus obtained was filtrated to remove insoluble matter by a membrane filter being 0.45 $\mu$m in mesh. Then, the filtrated solution was freeze-dried to obtain powdered inclusion compound (A) of oleanolic acid. Analyzing the inclusion compound for oleanolic acid by a gas chromatograph method as described below, it was found that the inclusion compound includes 109 mg/g of oleanolic acid. The water solution in which the inclusion compound of oleanolic acid was dissolved was transparent.

METHOD OF DETERMINING OF OLEANOLIC ACID USING GAS CHROMATOGRAPH

A predetermined weight of oleanolic acid which is accurately weighed as a specimen is dissolved in 20 ml of water and supplied with dilute hydrochloric acid to be made weak acidity. Next, after extracting oleanolic acid from the water solution with methylene chloride, the methylene chloride phase is removed under reduced pressure by rinsing. The remaining residue is dissolved with 2 ml of methanol and stirred at 65° C. for two hours by use of a reflux condenser with addition of 3 ml of benzene and 0.4 ml of solution of trimethylsilyl-diazomethane-hexane. Thereafter, the solution thus obtained is permitted to stand overnight under room temperature, and methanol is added to make 10 ml in volume on the next day, and then, analyzed by the calibration method using a gas chromatograph.

Operation conditions:
Column = SE-30.
Detector = FID.
Carrier Gas = $N_2$ 60 ml/min. (Fixed quantity).

Column Temperature=290° C.

EXAMPLE 2

Ten kinds of compounds, α-CD (made by Ensuiko Sugar Refining Co., Ltd.), γ-CD (made by Nakarai Chemicals Co., Ltd.), K-100 (α-CD =60%, β-CD =30%, made by Ensuiko Sugar Refining Co., Ltd.), $G_1$-α-CD, $G_1$-β-CD, $G_2$-γ-CD, $G_2$-β-MixCD ($G_2$-γ-CD=62%, $(G_2)_2$-γ-CD=31%, maltose=7%), ISO-ELEAT (branching CD=50%, all CD=80%) (made by Nikken Chemicals Co., Ltd.), dimethyl (DM)-β-CD (made by Wako Pure Chemical Industries Ltd.), hydroxypropyl (HP)-β-CD (made by Rocket Co., Ltd.), each weight being 1 g, were treated in the same manner as that in Example 1 noted above, to obtain powdered inclusion compounds. Among them, the inclusion compound of $G_1$-β-CD is formulated as (B). These inclusion compounds were analyzed for oleanolic acid by the aforementioned gas chromatograph method. The results of the analysis are shown in Table 2.

TABLE 2

| Content of oleanolic acid in powdered inclusion compounds | | |
|---|---|---|
| No | Kind of CD | Content of oleanolic acid (mg/g) |
| 1 | α-CD | — |
| 2 | γ-CD | 114 |
| 3 | K-100 | 54 |
| 4 | $G_1$-α-CD | — |
| 5 | $G_1$-β-CD | 122 |
| 6 | $G_2$-γ-CD | 147 |
| 7 | $G_2$-β MixCD | 117 |
| 8 | ISOELEAT | 31 |
| 9 | DM-β-CD | 86 |
| 10 | HP-β-CD | 111 |

EXAMPLE 3

Under the condition that 0.3 g of sodium hydrogencarbonate was added to 10 ml of solution in which methanol:water is 2:1 so as to be made alkali, and heated to be dissolved with addition of 0.2 g of oleanolic acid and 1 g of α-CD or $G_1$-α-CD. Next, each compound was homogenized at 12,000 rpm for 10 minutes, and thereafter, treated in the same manner as Example 1 described above. As a result, two kinds of powdered inclusion compounds were obtained. These inclusion compounds were analyzed for oleanolic acid by the gas chromatograph method. The results of the analysis are shown in Table 3.

TABLE 3

| Content of oleanolic acid in powdered inclusion compounds | | |
|---|---|---|
| No | Kind of CD | Content of oleanolic acid (mg/g) |
| 1 | α-CD | 188 |
| 2 | $G_1$-α-CD | 140 |

EXAMPLE 4

0.75 g of β-CD was treated in the same manner as that in Example 1 except that 0.15 g of suspended ursolic acid (reagent made by Sigma Co., Ltd.) was added to 12 ml of 3%-sodium hydrogencarbonate, consequently to obtain powdered inclusion compound (C) of Sigma Co., Ltd.

EXAMPLE 5

1 g of β-CD after being suspended in 15 ml of 3%-sodium hydrogencarbonate was treated in the same manner as that in Example 1 except that 0.2 g of hederagenin (reagent made by Indo Fine Chemicals Co., Ltd.). Consequently, powdered inclusion compound (D) of Sigma Co., Ltd. could be obtained. The results of analysis for the inclusion compound obtained in this Example are shown in Table 4 together with the compound (C) obtained in Example described just above.

TABLE 4

| Content of triterpenes in powdered inclusion compounds | | |
|---|---|---|
| No | Kind of Triterpenes | Kind of CD | Content of Oleanolic Acid (mg/g) |
| 1 | Ursolic Acid | β-CD | 37 |
| 2 | Hederagenin | β-CD | 87 |

COMPARATIVE EXAMPLE 1

As is clear from the following list of compositions, ribosome is used as a surface active agent. Then, oleanolic acid is dissolved in the solution of the compositions to obtain 100 ml of solution of oleanolic acid (E) (slightly opaque).

COMPOSITIONS OF SOLUTION OF OLEANOLIC ACID AND SURFACE ACTIVE AGENT

Ribosome: 2.0%
Paraben: 0.2%
Emulsion stabilizer: 1.0%
Oleanolic acid: 0.5%
Polyhydroxy alcohol: 10.0%

After mixing the aforementioned compositions to homogenize, refined water is added to make 100 ml of solution.

COMPARATIVE EXAMPLE 2

160 ml of oleanolic acid is dissolved in 100 ml of DMSO to obtain the solution of oleanolic acid (F).

EXPERIMENTAL EXAMPLE 1

Each stock solution of the aforementioned six specimens (A)–(F) which were produced in Examples 1–5 and Comparative Examples 1–2 was adjusted in volume to 0.8 mg/ml of triterpene and subjected to the experiment on the inhibition of growth of streptococcus mutans mutans (S. mutans) which is a bacteria capable of yielding enzyme delivered of insoluble glucan causing a carious tooth. The results of the experiment are represented in Table 5.

Experiment on the Inhibition of Growth of S. Mutans

Strain: S. mutans OMZ 176 strains (obtained from the medicine faculty of Hiroshima University)
Culture Medium: Berman culture medium In 10 ml of the culture medium which is added so as to make oleanolic acid having the prescribed concentration, 0.1 ml of seed bacteria having $10^8$/ml was inoculated and cultured at 37° C. for 18 hours. Then, the extinction of the culture solution at OD 660 nm was measured by use of a spectrophotometer to be analyzed.

TABLE 5

Suppression of the growth against S. mutans

| Specimen No. | Kind of triterpenes | Kind of CD or surface active agent | Concentration of triterpene (μg/ml) | | | | | | |
|---|---|---|---|---|---|---|---|---|---|
| | | | 80 | 40 | 20 | 10 | 5 | 2.5 | 1.25 |
| | Oleanolic acid | β-CD | − | − | − | − | + | + | + |
| | Oleanolic acid | G$_1$-β-CD | − | − | − | − | − | + | + |
| | Ursolic acid | β-CD | − | − | − | − | − | − | + |
| | Hederagenin | β-CD | − | − | + | + | + | + | + |
| | Oleanolic acid | Ribosome | + | + | + | + | + | + | + |
| | Oleanolic acid | DMSO | − | − | − | − | − | + | + |

+: S. mutans grown
−: S. mutans not grown

EXPERIMENTAL EXAMPLE 2

The six specimens used in the aforenoted Experimental Example were respectively adjusted in volume to 1.6 mg/ml of triterpene and subjected to the following experiment on the synthesis inhibition of insoluble glucan yielded from S. mutans causing a carious tooth. The results of the experiment are represented in Table 6 below.

Experiment on Synthesis Inhibition of Insoluble Glucan

The reaction which was carried out at 37° C. for two hours using reaction solutions which are made with addition of 0.1 ml of each of glucosyltransferase, 0.2M-phosphoric acid buffer solution (pH 6.0), 0.5M-sucrose soluvent, and oleanolic acid (concentration of oleanolic acid in reaction is 100 to 400 μg/ml) was finished after adding 0.2 ml of 0.25N-hydrochloric acid thereto. Next, each solution to which 1 ml of distilled water is further added was subjected to centrifugal washing at 2000 G to remove the soluble matter from the reaction mixture. The sediment resultantly made, i.e. insoluble glucan, was freeze-dried. After drying, the insoluble glucan was dissolved in 2 ml of 0.5N-sodium hydroxide and subjected to colorimetric determination by phenol-sulfuric acid methods. The rate of inhibition relative to the synthesized quantity of insoluble glucan thus controlled was calculated.

TABLE 6

Synthesis inhibition of insoluble glucan

| Specimen | Kind of triterpenes | Kind of CD or surface active agent | Concentration of triterpenes (μg/ml) | Rate of inhibition (%) |
|---|---|---|---|---|
| A | Oleanolic acid | β-CD | 100 | 61.0 |
| | | | 200 | 68.0 |
| | | | 400 | 85.0 |
| B | Oleanolic acid | G$_1$-β-CD | 100 | 31.0 |
| | | | 200 | 53.0 |
| | | | 400 | 76.0 |
| C | Ursolic acid | β-CD | 100 | 55.0 |
| | | | 200 | 78.0 |
| | | | 400 | 83.0 |
| D | Hederagenin | β-CD | 100 | 24.0 |
| | | | 200 | 35.0 |
| | | | 400 | 49.0 |
| E | Oleanolic acid | Ribosome | 100 | 0 |
| | | | 200 | 0 |
| | | | 400 | 0 |
| F | Oleanolic acid | DMSO | 100 | 17.0 |
| | | | 200 | 34.0 |
| | | | 400 | 64.0 |

EXAMPLE 6

Compositions of Mashed Bean Jam

Azuki bean: 400 g
Salt: A dash
Sugar: 400 g
Inclusion compound of oleanolic acid (A): 12.0 g The mashed bean jam was made from the compositions listed above by a common method except for use of the inclusion compound of oleanolic acid (Content of oleanolic acid was 2 mg/g).

EXAMPLE 7

Tea

Tea (canned tea "Gogo-no-kocha"): 200 ml
Inclusion compound of oleanolic acid (A): 0.8 g The inclusion compound of oleanolic acid mentioned above was added to the canned tea sold at a market to prepare 200 ml of tea with inclusion compound of oleanolic acid (H) (Content of oleanolic acid was 0.4 mg/ml).

EXAMPLE 8

Mouth Rinse

Ethanol: 6 g
Sodium hydrogencarbonate: 0.5 g
Glycerin: 15 g
Sodium lauryl sulfate: 0.3 g
Inclusion compound of oleanolic acid (A) : 0.4 g The aforementioned compositions were dissolved in distilled water to make 100 ml of mouth rinse (I) (Content of oleanolic acid was 0.4 mg/ml).

COMPARATIVE EXAMPLE 3

Mashed bean jam (J), tea (K) and mouth rinse (L) were made from the compositions used in Examples 6, 7 and 8, excluding the inclusion compound of oleanolic acid.

EXPERIMENTAL EXAMPLE 3

The six specimens of the mashed bean jam, tea and mouth rinse (G)–(L) prepared in Example 6, 7 and 8 and Comparative Example 2 each were subjected to an inhibition test on enzyme synthesizing insoluble glucan in the same manner as in Experimental Example 2 described above. The experimental results are shown in Table 7.

Adjustment of specimens : Specimens G and J were diluted with distilled water to five times in volume, thoroughly stirred and passed through a filter cloth with a 200 mesh. The filtrated solutions were applied for the test. The other specimens were used as they were.

TABLE 7

| Specimen | No | Olenolic acid ($\mu$g/ml) | Rate of inhibition (%) |
|---|---|---|---|
| Mashed Bean Jam | G | 100 | 61.0 |
| | J | 0 | 0 |
| Tea | H | 100 | 57.0 |
| | K | 0 | 0 |
| Mouth rinse | I | 100 | 60.0 |
| | L | 0 | 0 |

INDUSTRIAL APPLICABILITY

The water-soluble pentacyclic triterpene thus obtained is fully soluble in water with maintaining pharmacological functions of cariostatic, and therefore, can be used as compositions for use in the mouth, and can be added uniformly to, for example, toothpaste, gargle, mouth rinse and chewing gum with maintaining its active state. Also, it can be uniformly added to not only compositions for use in the mouth, but also food additives applicable jam, marmalade, sweet bean paste, confectionery, candies, drinks and other pharmaceuticals with maintaining its active state.

Products to which the inclusion composition of triterpene is added are not deteriorated with time and can maintain its pharmacological activity for long. Thus, by applying the present compositions for the mouth after meals, teeth can be prevented from decaying, and foods drinks which are free from tooth decay can be produced.

The pharmacological functions of triterpene are featured in that they can be exhibited sufficiently when the concentration thereof is as little as 100 $\mu$g/ml.

We claim:

1. Water-soluble pentacyclic triterpene composition made by subjecting a pentacyclic triterpene compound having pharmacological activity to inclusion in a cyclodextrin, wherein said composition retains the pharmacological activity of said pentacyclic triterpene.

2. The water-soluble pentacyclic triterpene composition set forth in claim 1 wherein said pentacyclic triterpene compound is a compound of amylin group.

3. The water-soluble pentacyclic triterpene composition set forth in claim 2 wherein said pentacyclic triterpene compound is oleanolic acid, ursolic acid or hederagenin of amylin group.

4. The water-soluble pentacyclic triterpene composition set forth in claim 1 characterized in that said pentacyclic triterpene compound is dried to be powdered after bringing the pentacyclic triterpene compound and cyclodextrins into contact with water to subject the pentacyclic triterpene compound to inclusion in cyclodextrins.

5. A food comprising the water-soluble pentacyclic triterpene composition set forth in claim 1.

6. A drink comprising the water-soluble pentacyclic triterpene composition set forth in claim 1.

7. A composition for use in the mouth comprising the water-soluble pentacyclic triterpene composition set forth in claim 1.

* * * * *